(12) United States Patent
Nagae

(10) Patent No.: US 9,435,881 B2
(45) Date of Patent: Sep. 6, 2016

(54) OBJECT INFORMATION ACQUISITION APPARATUS, DISPLAY METHOD, AND STORAGE MEDIUM

(71) Applicant: CANON KABUSHIKI KAISHA, Tokyo (JP)

(72) Inventor: Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 448 days.

(21) Appl. No.: 13/975,064

(22) Filed: Aug. 23, 2013

(65) Prior Publication Data

US 2014/0064021 A1 Mar. 6, 2014

(30) Foreign Application Priority Data

Aug. 28, 2012 (JP) ................................. 2012-187618

(51) Int. Cl.
*G03B 42/06* (2006.01)
*G01S 7/52* (2006.01)
(Continued)

(52) U.S. Cl.
CPC .......... *G01S 7/52046* (2013.01); *A61B 8/461* (2013.01); *A61B 8/463* (2013.01); *A61B 8/469* (2013.01);
(Continued)

(58) Field of Classification Search
CPC .......... G01S 7/52063; G01S 7/52074; G01S 15/8915; A61B 8/463; A61B 8/5207
USPC .......................................................... 367/11
See application file for complete search history.

(56) References Cited

U.S. PATENT DOCUMENTS

2002/0028994 A1 3/2002 Kamiyama
2007/0255136 A1 11/2007 Kristofferson et al.
(Continued)

FOREIGN PATENT DOCUMENTS

CN 101053521 A 10/2007
CN 102341723 A 2/2012
(Continued)

OTHER PUBLICATIONS

Magali Sasso and Claude Cohen-Bacrie, Medical Ultrasound Imaging using the Fully Adaptive Beamformer, IEEE International Conference on Acoustics, Speech, and Signal Processing, 2005, Proceedings, ICASSP '05, Mar. 18-23, 2005, Philadelphia, PA, vol. 2, pp. 489-492, IEEE, Piscataway NJ, 2005.
(Continued)

*Primary Examiner* — Mark Hellner
(74) *Attorney, Agent, or Firm* — Canon U.S.A. Inc., IP Division

(57) ABSTRACT

An object information acquisition apparatus according to the present invention includes a plurality of conversion elements configured to receive waves reflected at each position inside an object, and convert the reflected waves into a plurality of received signals, a fixed signal processing unit configured to apply addition with a predetermined weight to the plurality of received signals to acquire first distribution information, an adaptive signal processing unit configured to apply adaptive signal processing to the plurality of received signals to acquire second distribution information, and a display control unit configured to input the first distribution information and the second distribution information, and output image information to a display unit, wherein the display control unit outputs image information for displaying in parallel in the same screen an image of the first distribution information, an image of the second distribution information or a combined image of the first and second distribution information.

24 Claims, 9 Drawing Sheets

(51) Int. Cl.
*A61B 8/00* (2006.01)
*G01S 15/89* (2006.01)
*A61B 8/08* (2006.01)

(52) U.S. Cl.
CPC ......... *A61B 8/5207* (2013.01); *G01S 7/52047* (2013.01); *G01S 7/52074* (2013.01); *G01S 15/8915* (2013.01); *A61B 8/08* (2013.01); *A61B 8/5246* (2013.01)

(56) References Cited

U.S. PATENT DOCUMENTS

| | | | |
|---|---|---|---|
| 2008/0167557 A1* | 7/2008 | Kozai | A61B 8/06 600/441 |
| 2009/0299184 A1 | 12/2009 | Walker et al. | |
| 2010/0106017 A1 | 4/2010 | Shin et al. | |
| 2011/0306884 A1 | 12/2011 | Tanigawa et al. | |
| 2012/0022373 A1 | 1/2012 | Tateyama | |
| 2013/0286023 A1* | 10/2013 | Friedman | A61B 8/08 345/440 |

FOREIGN PATENT DOCUMENTS

| | | |
|---|---|---|
| CN | 102449499 A | 5/2012 |
| JP | 2001-212144 A | 8/2001 |
| JP | 2007-296329 A | 11/2007 |
| JP | 2009-297072 A | 12/2009 |
| JP | 2011-005237 A | 1/2011 |
| JP | 2011-224410 A | 11/2011 |
| JP | 2011-254962 A | 12/2011 |
| WO | 2010/100868 A1 | 9/2010 |
| WO | 2012/035723 A1 | 3/2012 |

OTHER PUBLICATIONS

Hirofumi Taki, Kousuke Taki, Takuya Sakamoto, Makoto Yamakawa, Tsuyoshi Shiina and Toru Sato, High Range Resolution Medical Acoustic Vacular Imaging with Frequency Domain Interferometry, 2010 Annual International Conference of the IEEE Engineering in Medicine and Biology Society (EMBC), Buenos Aires, AR, Aug. 31, 2010-Sep. 4, 2010, 1: 5298-5301, IEEE, Piscataway NJ, 2005.

* cited by examiner

OBJECT INFORMATION ACQUISITION APPARATUS, DISPLAY METHOD, AND STORAGE MEDIUM

BACKGROUND OF THE INVENTION

1. Field of the Invention

The present disclosure relates to an object information acquisition apparatus, a display method, and a storage medium. In particular, the present disclosure relates to a technique for transmitting elastic waves to an object, and displaying distribution information acquired by receiving reflected waves from the object.

2. Description of the Related Art

In an ultrasonograph which is an object information acquisition apparatus, the spatial resolution in the depth direction in image data formation based on the pulse echo method can be generally represented by (nλ)/2, where λ indicates the wavelength of ultrasonic waves and n indicates the number of transmission waves. For example, when the ultrasonograph transmits ultrasonic waves having a center frequency of 12 MHz for two wavelengths, the spatial resolution is about 0.13 mm.

The pulse echo method will be described below. When the ultrasonograph transmits ultrasonic pulses (elastic waves) to an object, the ultrasonic waves are reflected by the object according to the acoustic impedance difference between tissues inside the object, and return to the ultrasonograph. Then, the ultrasonograph receives the reflected waves and generates image data by using received signals of the reflected waves. Typically, the ultrasonograph applies delay and sum to the received signals, acquires an envelope, and converts the envelope into luminance values to generate image data. Repeating ultrasonic wave transmission and reception in a plurality of directions or positions inside the object enables acquiring luminance information on a plurality of scanning lines in the directions in which ultrasonic wave transmission and reception were made. Arranging the luminance information on the plurality of scanning lines enables imaging an inside of the object.

It is common that the ultrasonograph adds a temporal deviation to received signal waveforms between elements by using a plurality of conversion elements for converting the ultrasonic wave into an electrical signal for focusing inside the object both for transmission and reception.

On the other hand, applying adaptive signal processing, which has developed in the field of the radar, together with ultrasonic waves enables improving the spatial resolution. M. SASSO et al., Medical Ultrasound Imaging Using The Fully Adaptive Beamformer, Proc. Acoustics and Speech Signal Process. volume. 2, pp. 489-492 (March 2005 discusses a technique using the Capon method (adaptive signal processing) to improve the spatial resolution in the direction perpendicular to the depth direction (direction perpendicular to the scanning line direction).

As a technique for improving the spatial resolution in the depth direction (scanning line direction), Hirofumi Taki, Kousuke Taki, Takuya Sakamoto, Makoto Yamakawa, Tsuyoshi Shiina and Toru Sato: Conf Proc IEEE Eng Med Biol Soc. 2010; 1: 5298-5301 discusses results of imaging of the layer structure of the blood vessel wall by applying the Frequency Domain Interferometry (FDI) method and the Capon method (adaptive signal processing). Applying the FDI method and the Capon method to received signals enables improving the spatial resolution in the depth direction. However, it is assumed that a plurality of reflective layers exists in a signal range (within a processing range) in the depth direction clipped for the FDI processing. A plurality of reflected waves from close reflective layers is highly likely to have high mutual correlations. It is known that applying adaptive signal processing, such as the Capon method, to received signals of a plurality of reflected waves having such high correlations will cause an unexpected operation, such as negating a desired signal. By using the frequency averaging technique to reduce (suppress) the effect caused by signals (correlated interference waves) having such correlations, the FDI method and the Capon method are applicable to the received signals of the reflected waves.

Applying adaptive signal processing, such as a method combining the FDI and Capon methods, enables improving the spatial resolution of an image. However, if an image generated by such a new technique is displayed, a user (particularly, a doctor) may feel odd since the user is familiar with the conventional B mode image (an image produced by applying delay and sum to a plurality of received signals to acquire an envelope, and converting the envelope into luminance values). In particular, if only an image generated through adaptive signal processing is displayed, the odd feeling may increase.

SUMMARY OF THE INVENTION

An embodiment of the present invention is directed to providing a user-friendly display method and object information acquisition apparatus used when displaying an image generated through adaptive signal processing.

According to an aspect of the present invention, an object information acquisition apparatus includes a plurality of conversion elements configured to transmit elastic waves to an object, receive waves reflected at each position inside the object, and convert the reflected waves into a plurality of received signals; a fixed signal processing unit configured to apply addition with a predetermined weight to the plurality of received signals to acquire first distribution information; an adaptive signal processing unit configured to apply adaptive signal processing to the plurality of received signals with a weight adaptively changing according to the received signals to acquire second distribution information; and a display control unit configured to input the first distribution information and the second distribution information, and output image information to a display unit, wherein the display control unit outputs image information for displaying in parallel in the same screen an image of the first distribution information, and an image of the second distribution information or a combined image of the first and second distribution information.

According to another aspect of the present invention, a display method displays an image on a display unit by using distribution information acquired by an object information acquisition apparatus, wherein the acquired distribution information includes first distribution information acquired by applying addition with a predetermined weight to a plurality of received signals acquired by transmitting elastic waves to an object and receiving reflected waves reflected by the object, and second distribution information obtained by applying to the plurality of received signals adaptive signal processing with a weight which adaptively changes according to the received signals, wherein the image of the first distribution information, and the image of the second distribution information or the combined image of the first and second distribution information are displayed in parallel in the same screen.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Figure 1:
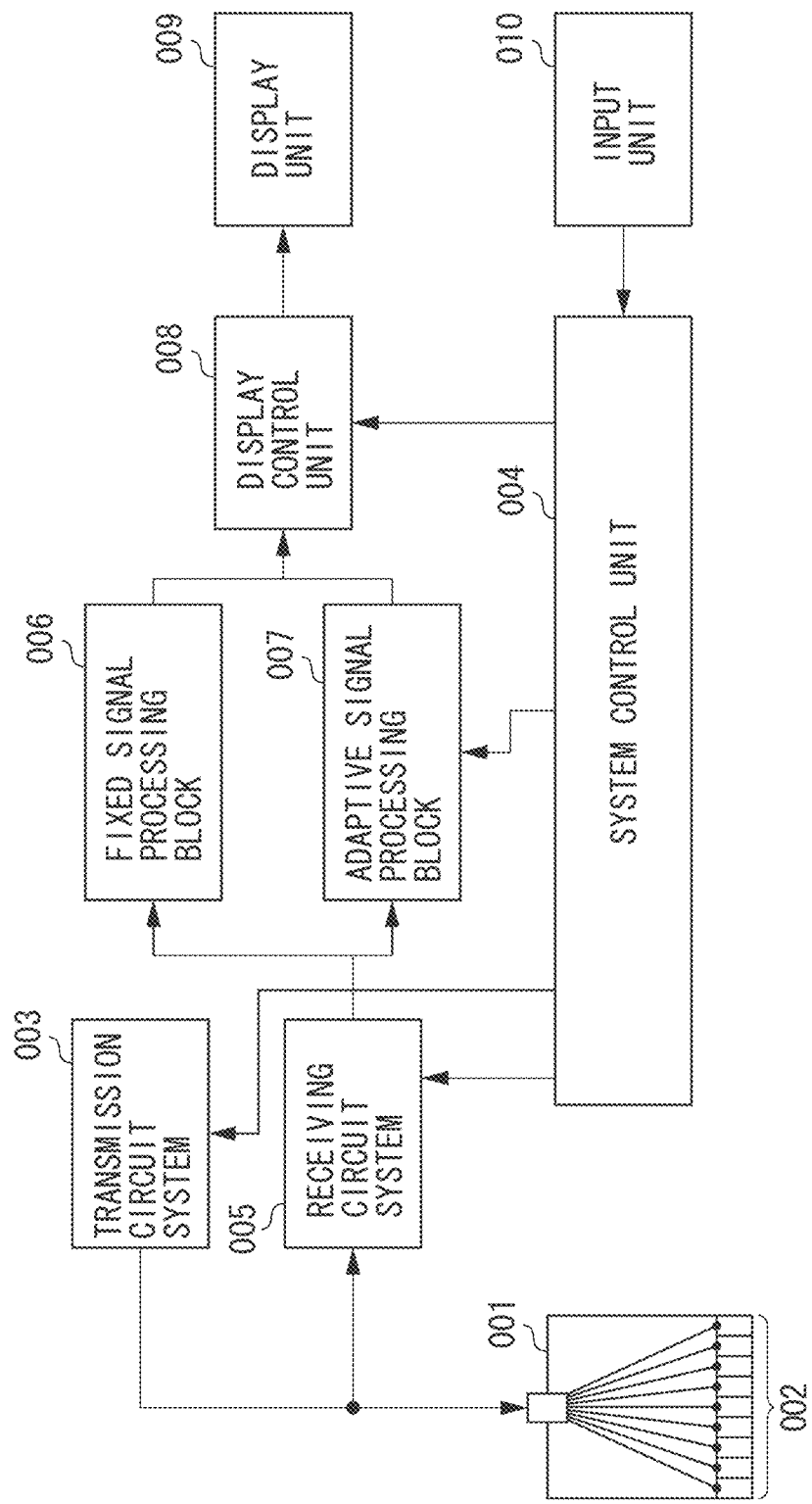
FIG. 1 schematically illustrates an overview of an object information acquisition apparatus according to the present invention.

Various exemplary embodiments, features, and aspects of the invention will be described in detail below with reference to the drawings.

Exemplary embodiments of the present invention will be described below with reference to the accompanying drawings. Basically, identical elements are assigned the same reference numeral, and redundant descriptions will be omitted.

In an embodiment of the present invention, an elastic wave typically refers to an ultrasonic wave and includes what is called sound wave, ultrasonic wave, or acoustic wave. The object information acquisition apparatus according to an embodiment of the present invention includes an apparatus which transmits elastic waves to an object, receives reflected waves (reflected elastic waves) reflected inside the object, and acquires inside-object distribution information as image data. The acquired inside-object distribution information is information reflecting the acoustic impedance difference between tissues inside the object. In an embodiment of the present invention, the scanning line indicates a virtual line formed in the traveling direction of elastic waves transmitted from a probe 001.

The first exemplary embodiment will be described below centering on a basic apparatus configuration and processing flow according to an embodiment of the present invention.
Basic Configuration of Object Information Acquisition Apparatus A configuration of an object information acquisition apparatus according to the present exemplary embodiment of the invention will be described below with reference to FIG. 1. FIG. 1 schematically illustrates an overview of the object information acquisition apparatus according to the present exemplary embodiment of the invention. The object information acquisition apparatus according to the present exemplary embodiment includes a probe 001 having a plurality of conversion elements 002, a receiving circuit system 005, a transmission circuit system 003, a fixed signal processing block 006, an adaptive signal processing block 007, and a display control unit 008 The object information acquisition apparatus according to the present exemplary embodiment further includes a display unit 009, an input unit 010, and a system control unit 004.

The probe 001 is a receiver transmitter which transmits elastic waves to a plurality of positions inside the object, and receives reflected waves. The probe 001 includes the plurality of conversion element 002 for converting elastic waves into electrical signals.

The transmission circuit system 003 is a transmission signal generation unit for generating, based on a control signal from the system control unit 004, a plurality of transmission signals having a delay time and an amplitude for each target position and each target direction. The plurality of conversion elements 002 converts the transmission signals into elastic waves, and the probe 001 transmits the elastic waves to the object as elastic wave beams. The plurality of conversion elements 002 also receives elastic waves (reflected waves) reflected by a subject inside the object (reflective interface and reflector), and converts the elastic waves into a plurality of received signals. The receiving circuit system 005 inputs the received signals.

The receiving circuit system 005 is a received signal processing unit for amplifying the plurality of received signals and converting the received signals into a plurality of digital signals (digitized received signals). In the an embodiment of present invention, not only received analog signals output by the conversion elements 002 but also signals that have undergone amplification and digital conversion are referred to as received signals. The fixed signal processing block 006 and the adaptive signal processing block 007 input the plurality of digital signals output from the receiving circuit system 005.

Figure 2:
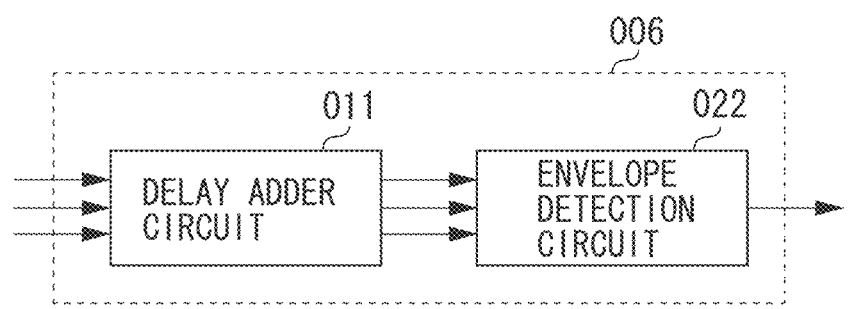
FIG. 2 schematically illustrates a configuration of a fixed signal processing block.

The fixed signal processing block 006 is equivalent to a fixed signal processing unit according to an embodiment of the present invention. FIG. 2 illustrates a configuration of the fixed signal processing block 006. In the fixed signal processing block 006, a delay and sum circuit 011 (delay and sum unit) applies delay processing to the plurality of digital signals according to transmission directions and positions of the elastic waves, and applies addition to the plurality of delay-applied digital signals. Namely, delay and sum processing is carried out. A plurality of scanning line signals is acquired through the delay and sum processing. The fixed signal processing block 006 may multiply each of the plurality of digital signals by a weight before applying addition to the digital signals. Although the weight changes according to an observation position and transmission and reception conditions, a predetermined (fixed) weight is used in many cases. Phasing addition generates signals corresponding to the sound pressure of the waves reflected at respective positions inside the object, as scanning line signals. Then, the envelope detection circuit 012 (envelope detection unit) performs envelope detection by using the plurality of scanning line signals to acquire first distribution information. The fixed signal processing block 006 outputs the acquired first distribution information to the display control unit 008.

The adaptive signal processing block 007 is equivalent to an adaptive signal processing unit according an embodiment of to the present invention. Adaptive signal processing adaptively changes processing parameters according to the received signals. In particular, the Capon method (also referred to as Constrained Minimization of Power (CMP)), one of adaptive signal processing methods, is applied to a plurality of input signals so that the electric power is minimized with fixed sensitivity for the target directions and target positions. Such adaptive signal processing has an effect of improving the spatial resolution. The adaptive signal processing block 007 outputs as second distribution information the power distribution having an improved resolution in at least one of the depth direction and the direction perpendicular to the depth direction. The depth direction refers to the traveling direction of the elastic waves (ultrasonic beams) transmitted from the probe 001, and is the scanning line direction. Adaptive signal processing will be described in detail below with reference to FIGS. 3A, 3B, and 3C.

The display control unit 008 inputs the first distribution information from the fixed signal processing block 006, and the second distribution information from the adaptive signal processing block 007. The display control unit 008 outputs image information to be displayed on the display unit 009. The display unit 009 displays an image indicating inside-object distribution information based on the image information output from the display control unit 008. The processing performed by the display control unit 008 will be described in detail below with reference to FIG. 4. The display control unit 008 applies various image processing, such as edge emphasis and contrast adjustment to image information of the first distribution information, image information of the second distribution information, and combined image information of the first and second distribution information, and outputs image information of luminance data.

According to the present invention, the fixed signal processing block 006, the adaptive signal processing block 007, the display control unit 008, and the system control unit 004 are configured by a processing device such as a central processing unit (CPU), a graphics processing unit (GPU), or a field programmable gate array (FPGA) chip. The display unit 009 displays an image based on the image information input from the display control unit 008. The display unit 009 is a liquid crystal display (LCD), a cathode ray tube (CRT), or an organic electroluminescence (EL) display.

The input unit 010 is used by a user to input a specified area. The user specifies a predetermined area by using the input unit 010, referring to an image of the first distribution information displayed on the display unit 009. The input unit 010 is a pointing device, such as a mouse and a keyboard, a pen tablet, or a touchpad attached to the surface of the display unit 009. The display unit 009 and the input unit 010 may be separately prepared and connected to the object information acquisition apparatus according to an embodiment of the present invention, instead of being included in the object information acquisition apparatus according to an embodiment of the present invention.

(Details of Adaptive Signal Processing)

Figure 3A:
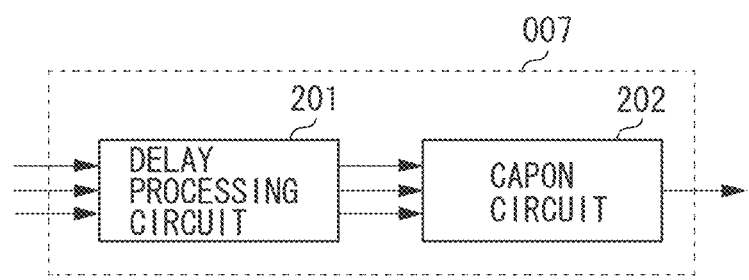
FIGS. 3A, 3B, and 3C schematically illustrate different configurations of an adaptive signal processing block.
Figure 3B:
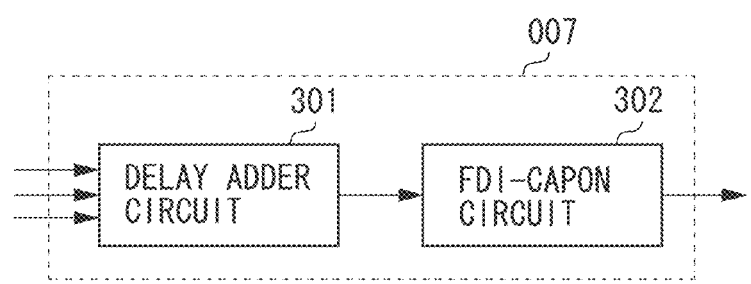
Figure 3C:
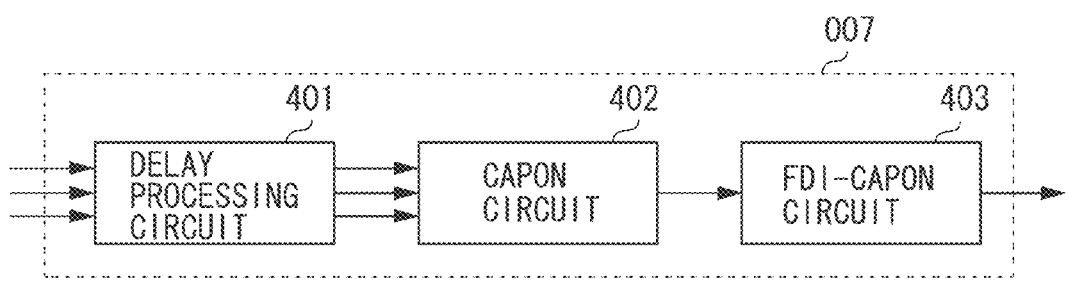

Processing performed by the adaptive signal processing block 007 of an embodiment of the present invention will be described below. FIGS. 3A, 3B, and 3C illustrate three different configurations of the adaptive signal processing block 007. Example configurations of the adaptive signal processing block 007 according to an embodiment of the present invention will be described below with reference to FIGS. 3A, 3B, and 3C.

FIG. 3A illustrates a configuration of the adaptive signal processing block 007 for improving the resolution in the direction perpendicular to the depth direction (traveling direction of the elastic waves (ultrasonic beams) transmitted from the probe 001). Proc. Acoustics, Speech Signal Process. pp. 489-492 (March 2005) discusses a technique of such adaptive signal processing for improving the resolution in the direction perpendicular to the depth direction.

Processing performed when adaptive signal processing is applied to the plurality of received signals will be described below based on the Capon method.

Processing for calculating a correlation matrix based on the plurality of received signals will be described below. First of all, the delay processing circuit 201 applies the Hilbert transform and the delay processing (phasing) according to target positions to the plurality of received signals output from the plurality of conversion elements 002. The received signals are calculated in the complex notation in this way. When the s-th sample of a signal obtained by processing a received signal from the k-th element is xk[s], an input vector X[s] of the s-th sample is defined by the following formula.

$$X[s] = [x_1[s], x_2[s], \ldots, x_M[s]]^T \quad (1)$$

where M indicates the number of elements.

Then, a Capon circuit 202 (adaptive signal processing unit) calculates a correlation matrix $R_{xx}$ by using the input vector X[s].

$$R_{xx} = E[X[s]X^H[s]] \quad (2)$$

$$= \begin{bmatrix} E[x_1[s]x_1^*[s]] & E[x_1[s]x_2^*[s]] & \ldots & E[x_1[s]x_M^*[s]] \\ E[x_2[s]x_1^*[s]] & E[x_2[s]x_2^*[s]] & \ldots & E[x_2[s]x_M^*[s]] \\ \vdots & \vdots & \ddots & \vdots \\ E[x_M[s]x_1^*[s]] & E[x_M[s]x_2^*[s]] & \ldots & E[x_M[s]x_M^*[s]] \end{bmatrix}$$

A superscript H in formula (2) indicates a complex conjugate transposition, and a superscript * indicates a complex conjugate. E[•] indicates processing for calculating a time average, processing for varying the sample number (s in this case) and calculating an average.

Then, to suppress the effect of a correlated interference wave which reaches the probe 001 from a direction other than the target directions, the Capon circuit 202 applies the spatial average method to the correlation matrix $R_{xx}$ to obtain an average correlation matrix $R'_{xx}$.

$$R'_{xx} = \sum_{n=1}^{M-K+1} z_n R^n_{xx} \quad (3)$$

$R^n_{xx}$ indicates a partial matrix in the correlation matrix $R_{xx}$, moving along the diagonal elements of $R_{xx}$. Specifically, $R^n_{xx}$ is a matrix having a size of K×K, positioned so that the (n, n) element of $R_{xx}$ becomes the first diagonal element of $R^n_{xx}$. $Z_n$ indicates a coefficient used when adding respective partial matrices, and is adjusted so that the sum total of $Z_n$ equals 1.

The Capon method obtains a complex weight for minimizing the output power under certain restriction conditions. The complex weight refers to a weight represented by a complex vector. With the Capon method, a complex weight $W_{opt}$ for minimizing the output power, with the sensitivity for the received signals of the elastic waves from the target directions constrained to 1, can be calculated by the following formula.

$$W_{opt} = \gamma R_{xx}'^{-1} C, \quad \gamma = \frac{1}{C^H R_{xx}'^{-1} C} \quad (4)$$

C indicates a constraint vector and varies corresponding to the element positions and target directions. However, when the phasing delay processing has been applied to the received signals, C may be a vector all having a value of 1 with respect to the size (K in this case) of the average correction matrix.

A calculated electric power $P_{min}$ can be obtained as follows by using the complex weight $W_{opt}$. The calculated electric power $P_{min}$ indicates distribution information (information about distribution related to acoustic characteristics) reflecting the acoustic impedance difference among tissues inside the object according to the present exemplary embodiment.

$$P_{min} = \frac{1}{2} \frac{1}{C^H R_{xx}'^{-1} C} \quad (5)$$

The Capon circuit 202 can acquire a correlation matrix and further an average correlation matrix based on the received signals, and, by using an inverse matrix, acquire a complex weight and a power distribution when the complex weight is used. The complex weight, and the electric power obtained by using the complex weight are a complex weight and an electric power when the sensitivity to signals of the elastic waves from the target directions is set to 1, and signals of the elastic waves reaching from other directions are suppressed. In other words, the Capon method enables selectively extracting signals of the elastic waves from the target directions, improving the spatial resolution in the direction perpendicular to the depth direction as the result. The electric power can also be calculated by applying QR decomposition and backward substitution to the average correlation matrix, without directly obtaining an inverse matrix.

The adaptive signal processing block 007 applies adaptive signal processing (using the Capon method) to the plurality of received signals in this way with a weight which adaptively changes corresponding to the received signals. As a result, the adaptive signal processing block 007 outputs the power distribution (equivalent to the second distribution information) having an improved resolution in the direction perpendicular to the depth direction.

A second example configuration of the adaptive signal processing block 007 will be described below with reference to FIG. 3B. FIG. 3B illustrates a configuration of the adaptive signal processing block 007 for improving the resolution in the depth direction (traveling direction of the elastic waves (ultrasonic beams) transmitted from the probe 001). As a technique for improving the spatial resolution in the depth direction, adaptive signal processing is combined with the Frequency Domain Interferometry (FDI) method. Hirofumi Taki, Kousuke Taki, Takuya Sakamoto, Makoto Yamakawa, Tsuyoshi Shiina and Toru Sato: Conf Proc IEEE Eng Med Biol Soc. 2010; 1: 5298-5301 discusses a technique in which the FDI method and the Capon method (adaptive signal processing) are applied.

The FDI method decomposes the received signals into frequency components, and varies the phase of the decomposed signals corresponding to the target positions to presume the received electric power at the target positions. Phase variation can be predetermined based on the product of the distance from a certain reference position to the target positions and the number of waves corresponding to the frequency.

Specifically, a method combining the FDI method and adaptive signal processing will presume the received electric power at the target positions by using phase variation and weight calculated depending on each signal through adaptive signal processing, instead of predetermined fixed phase variation and weight, with respect to each received signal decomposed into frequency components.

When applying the frequency averaging technique to the received signals of the elastic waves having a wide frequency band such as pulse waves, it is preferable to apply whitening to the received signals based on a reference signal.

Referring to FIG. 3B, the delay and sum circuit 301 (delay and sum unit) applies the delay processing to the plurality of digital signals according to the transmission direction and position of the elastic waves, and applies delay and sum to the plurality of digital signals after the delay processing. Similar to the delay and sum in the fixed signal processing block 006, delay and sum generates signals corresponding to the sound pressure of the reflected waves reflected at respective positions inside the object, as scanning line signals.

Then, an FDI-Capon circuit 302 (FDI adaptive processing unit) receives the plurality of scanning line signals output from the delay and sum circuit 301 as input signals. Then, the FDI-Capon circuit 302 extracts signals for the time interval of one unit of processing, i.e., the processing range, based on the plurality of scanning line signals.

Then, the FDI-Capon circuit 302 applies the Fourier transform to the extracted signals to decompose the signals into frequency components ($X_{s1}, X_{s2}, X_{s3}, \ldots$, and $X_{sN}$). In the meantime, the FDI-Capon circuit 302 inputs at least one reference signal from a reference signal storage unit (not illustrated). Then, the FDI-Capon circuit 302 applies the Fourier transform to the reference signal to decompose the reference signal into frequency components ($X_{r1}, X_{r2}, X_{r3}, \ldots, X_{rN}$).

Then, the FDI-Capon circuit 302 performs whitening represented by the following formula.

$$X_{wk} = \frac{X_{sk} X_{rk}^*}{|X_{rk}|^2 + \eta} \quad (6)$$

$X_{wk}$ (k=1, 2, ..., N) indicates frequency components, $\eta$ indicates a minute amount for stabilization of calculation, and * indicates a complex conjugate, after whitening. Then, the FDI-Capon circuit 302 calculates a correlation matrix R by using a vector $X_f$ having frequency components that have undergone whitening.

$$X_f = [X_{W1}, X_{W2}, \ldots, X_{WN}]^T$$

$$R = X_f X_f^{T*}$$

T indicates transposition. The correlation matrix R is a matrix having a size of N×N. Then, the FDI-Capon circuit 302 extracts partial matrices from the correlation matrix R, and applies the frequency averaging technique to respective partial matrices for averaging.

$$R' = \frac{1}{M} \sum_{m=1}^{M} R_m \quad (7)$$

-continued $$R_{mij} = X_{W(i+m-1)} X^*_{W(j+m-1)}$$

R' indicates a frequency average correlation matrix. $R_m$ indicates a partial matrix of the correlation matrix, and has elements $R_{mij}$. Thus, the FDI-Capon circuit 302 calculates the frequency average correction matrix R'.

Then, the FDI-Capon circuit 302 inputs the constraint vector C. The constraint vector C varies corresponding to a position r within the processing range, and is defined by the following formula.

$$C=[\exp(jk_1 r), \exp(jk_2 r), \ldots, \exp(jk_{(N-M+1)} r)]$$

The FDI-Capon circuit 302 calculates a power distribution P(r) in the processing range by using the frequency average correction matrix R' and the constraint vector C. The calculated power distribution P(r) indicates distribution information (information about distribution related to the acoustic characteristics) reflecting the acoustic impedance difference between tissues inside the object according to the present exemplary embodiment.

$$P(r) = \frac{1}{C^{T*}(R' + \eta' E)^{-1} C} \quad (8)$$

$\eta' E$ indicates a diagonal matrix added to stabilize the inverse matrix calculation.

In the present exemplary embodiment, the adaptive signal processing block 007 applies the FDI method and adaptive signal processing (in this case by using the Capon method) to the plurality of received signals in this way. As a result, the adaptive signal processing block 007 outputs the power distribution (equivalent to the second distribution information) with an improved resolution in the depth direction.

A third example configuration of the adaptive signal processing block 007 will be described below with reference to FIG. 3C. A delay processing circuit 401 applies the Hilbert transform and the delay processing according to the target positions, to the plurality of received signals output from the plurality of conversion elements 002, and outputs digital signals. A Capon circuit 402 inputs the digital signals that have undergone the delay processing, and performs the Capon processing. The Capon circuit 402 performs similar processing to the above-described processing (redundant description will be omitted), and eventually outputs a signal Y[s] calculated by the following formula. X'[s] indicates a vector extracted from the input vector X[s] of the s-th sample, which is in the size of the complex weight $W_{opt}$.

$$Y[s] = W_{opt}^H X'[s] \quad (9)$$

The output Y[s] holds phase information of the reflected waveforms corresponding to the target positions, enabling performing subsequent FDI-Capon processing. The FDI-Capon circuit 302 applies the FDI-Capon processing to the input signal Y[s], and outputs the power distribution.

Performing such processing enables acquiring a power distribution with improved resolutions in the depth direction and in the direction perpendicular to the depth direction.

Although the processing of the Capon method has specifically been described as an example of adaptive signal processing, similar effects of an embodiment of the present invention can also be obtained by using other adaptive signal processing, such as the MUSIC method and the ESPRIT method.

(Display Method)

Figure 4:
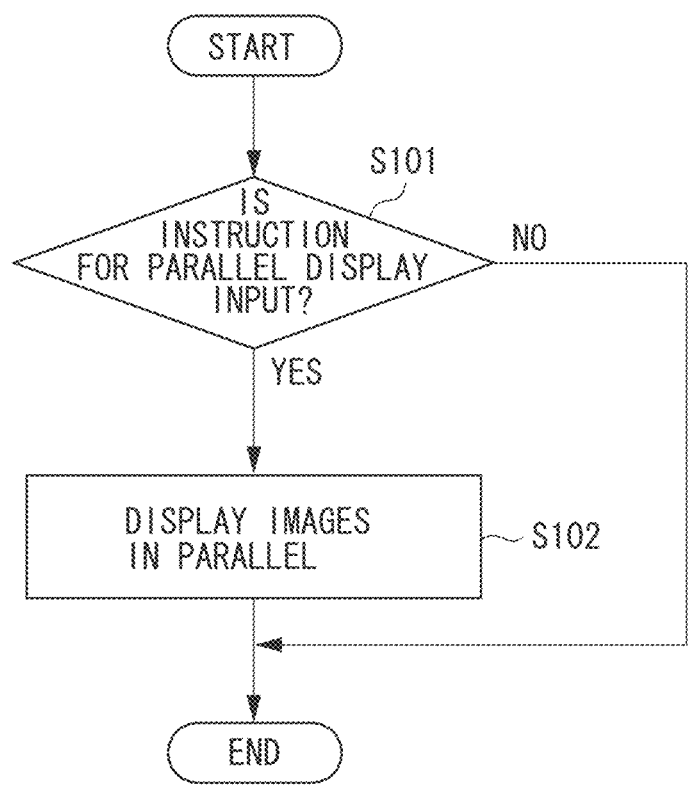
FIG. 4 is a flowchart illustrating processing of a display method according to a first exemplary embodiment.

Processing performed by a display method according to the present exemplary embodiment will be described below with reference to FIG. 4. FIG. 4 is a flowchart illustrating the display method according to the present exemplary embodiment.

Instep S101, the display control unit 008 determines whether an instruction for parallel display of images illustrating the inside-object distribution information (parallel display instruction information) is input from the user. For example, it is preferable to input a parallel display instruction when the user clicks a PARALLEL DISPLAY button (see FIGS. 5A and 5B) displayed in the screen in the display unit 009.

When a parallel display instruction is input (YES in step S101), then in step S102, the display control unit 008 outputs image information for displaying in parallel in the same screen the image of the first distribution information, an image of the second distribution information, and the image combining the first and second distribution information (hereinafter referred to as a combined image of the first and second distribution information). The display unit 009 displays these images in parallel based on the image information. The present exemplary embodiment will be described below about a case where the image of the first distribution information and the image of the second distribution information are displayed in parallel. Display of a combined image of the first and second distribution information will be described in a fourth exemplary embodiment (describe below).

Figure 5A:
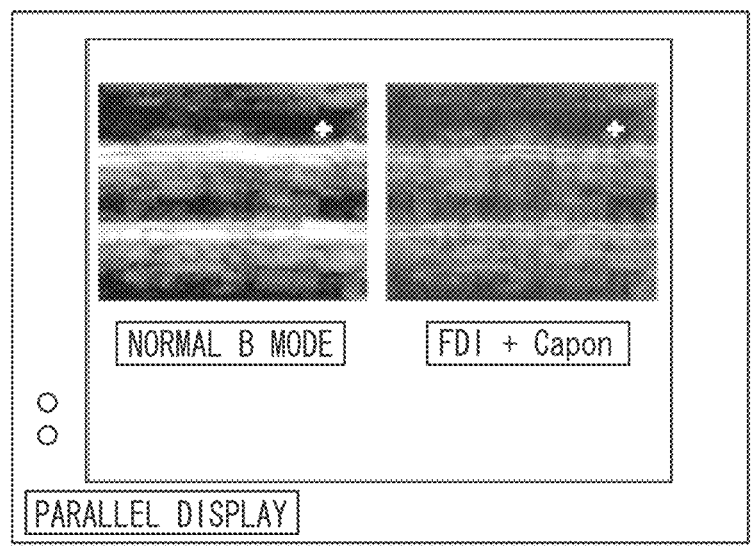
FIGS. 5A and 5B illustrate example screens displayed on a display unit according to the first exemplary embodiment.
Figure 5B:
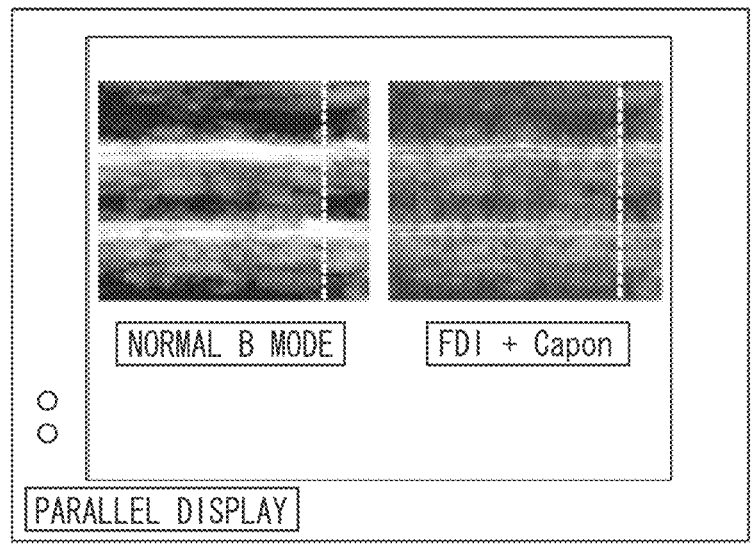

FIGS. 5A and 5B illustrate example screens displayed on the display unit 009 according to the present exemplary embodiment, i.e., the layer structure of the blood vessel wall. In the examples illustrated in FIGS. 5A and 5B, the adaptive signal processing block 007 performs processing combining the FDI method and the Capon method (the example illustrated in FIG. 3B) as adaptive signal processing to acquire an image of the second distribution information.

In the examples illustrated in FIGS. 5A and 5B, the screen displays the PARALLEL DISPLAY button. When the user clicks the PARALLEL DISPLAY button to turn ON the parallel display mode, the display control unit 008 inputs an instruction for displaying in parallel the image of the first distribution information and the image of the second distribution information. The parallel display mode can be turned ON when the user clicks the PARALLEL DISPLAY button in a state where the first and second distribution information are input to the display control unit 008. The user may click the PARALLEL DISPLAY button before the first and second distribution information are input.

As illustrated in FIGS. 5A and 5B, the image of the second distribution information on the right hand side (FDI+Capon) has a higher resolution in the depth direction than the image of the first distribution information on the left-hand side (normal B mode). Specifically, FDI+Capon provides a sharper image of the blood vessel wall than the normal B mode.

As in the present exemplary embodiment, displaying in parallel the image of the second distribution information and the image of the first distribution information can reduce user's odd feeling.

In the present exemplary embodiment, the display unit 009 displays guides for associating a position within the image of the first distribution information, with a position within the image of the second distribution information. In other words, the display unit 009 displays guides for displaying an identical position inside the object within the image of the second distribution information and within the image of the first distribution information. Specifically, referring to FIG. 5A, the display unit 009 displays cross-shaped marks as guides for associating a predetermined position within the image of the first distribution information with a position corresponding to the predetermined position within the image of the second distribution information, thus indicating an identical position inside the object. FIG. 5B illustrates an identical position inside the object in each image by using dotted-line guides.

However, in the present exemplary embodiment, since hiding the guides which associate the positions may improve image visibility, it is preferable that the user can select either one of a mode in which the position associating guides are displayed and a mode in which the position associating guides are not displayed. For example, it is preferable to display on the screen a button for turning guide display ON and OFF.

It is preferable that, in addition to the above-described parallel display mode in which images are displayed in parallel, the display control unit 008 provides either one of a single display mode and a superimposed display mode. In other words, it is possible for the display control unit 008 to change the parallel display mode to the single display mode or the superimposed display mode. The user can select from these modes the display mode to be executed first. The single display mode singly displays any one of the image of the first distribution information, the image of the second distribution information, and the combined image of the first and second distribution information. The superimposed display mode displays the image of the first distribution information, and the image of the second distribution information (or the combined image of the first and second distribution information) in the same display area in a superimposed way. Providing different display modes in addition to the parallel display mode in this way increases the user-friendliness. When changing the display mode, for example, the user clicks a mode change button displayed on the screen of the display unit 009 to select a desired display mode. The display control unit 008 receives a mode selection from the user, and outputs the image information for the selected display mode.

Although, in the present exemplary embodiment, the image of the second distribution information is displayed in parallel with the image of the first distribution information, the effect of an embodiment of the present invention can also be obtained by displaying the combined image of the first and second distribution information in parallel with the image of the first distribution information.

A second exemplary embodiment differs from the first exemplary embodiment in that images are displayed in the display unit 009 in an arrangement determined according to adaptive signal processing. An object information acquisition apparatus according to the present exemplary embodiment has a similar configuration to that of the object information acquisition apparatus illustrated in FIG. 1. Since the overview of the display method is basically the same as the processing described with reference to FIG. 4, the following describes display processing different from that according to the first exemplary embodiment, with reference to FIG. 6.

In the present exemplary embodiment, the display control unit 008 changes the arrangement of images in parallel display depending on whether adaptive signal processing for generating the second distribution information is processing for improving the resolution in the depth direction or processing for improving the resolution in the direction perpendicular to the depth direction. In other words, the display control unit 008 changes the arrangement of images in parallel display depending on whether the adaptive signal processing applied to a plurality of received signals is processing for minimizing the electric power by fixing sensitivity for the target directions (Capon method) or processing for minimizing the electric power by fixing sensitivity for the target positions in the depth direction (a method combining the Capon and FDI methods).

Figure 6:
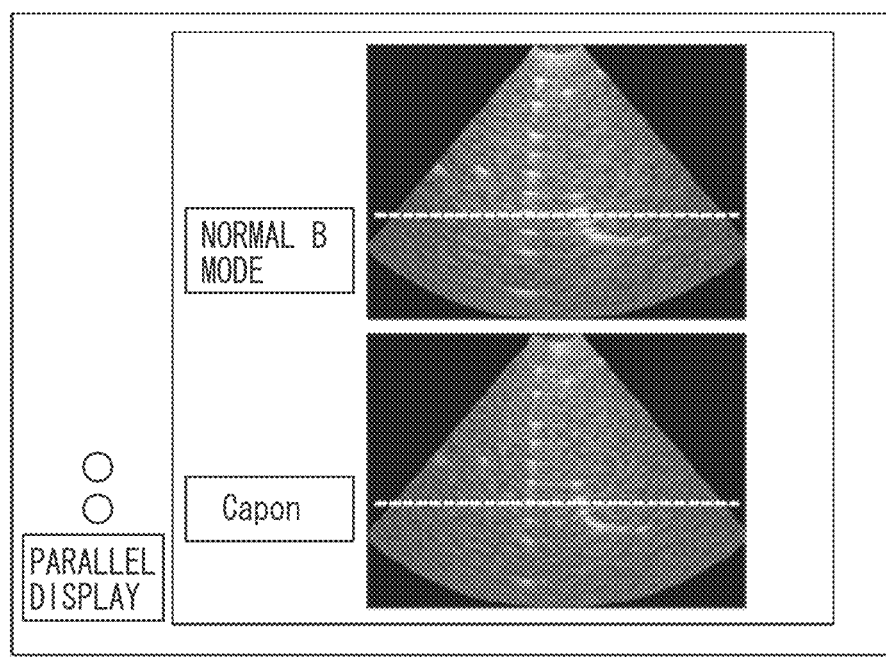
FIG. 6 illustrates an example screen displayed on the display unit according to a second exemplary embodiment.

FIG. 6 illustrates an example screen displayed on the display unit 009 according to the present exemplary embodiment. Referring to FIG. 6, the display unit 009 displays the image of the second distribution information acquired by using the Capon method as adaptive signal processing below the image of the first distribution information, in order to improve the resolution in the direction perpendicular to the depth direction. In other words, the display unit 009 displays in parallel the image of the first distribution information and the image of the second distribution information so that the two images are vertically arranged on the screen when viewed from the user. In the present exemplary embodiment, the vertical direction refers to the same direction as the depth direction in the image of the second distribution information (or in the combined image). Since the Capon method for improving the resolution in the direction perpendicular to the depth direction is used as adaptive signal processing, if the images are vertically arranged, image visibility can be improved for the user to a further extent. For example, when comparing the images of the first and second distribution information at the same position, and when the resolution in the direction perpendicular to the depth direction is higher than the resolution in the depth direction, the vertical arrangement of the two distribution information makes it easier to compare the positions in the direction perpendicular to the depth direction than the horizontal arrangement.

When the method combining the Capon and FDI methods is used as adaptive signal processing, it is preferable to display an acquired image of the second distribution information to the side of the image of the first distribution information, as illustrated in FIGS. 5A and 5B. In the present exemplary embodiment, the horizontal direction refers to the direction intersecting with the depth direction (typically, perpendicularly intersecting therewith) in the image of the second distribution information (or in the combined image). In other words, it is preferable to horizontally display the images of the first and second distribution information in parallel when viewed from the user. Since the method combining the Capon and FDI methods to improve the resolution in the depth direction is used as adaptive signal processing, horizontally arranging the images enables improving image visibility for the user to a further extent. For example, when comparing the images of the first and second distribution information at the same position, and when the resolution in the depth direction is higher than the resolution in the direction perpendicular to the depth direction, the horizontal arrangement of the two distribution information makes it easier to compare the positions in the depth direction than the vertical arrangement.

Changing the arrangement direction of images in parallel display according to adaptive signal processing in this way enables improving image visibility for the user to a further extent.

Also in the present exemplary embodiment, dotted lines are displayed as guides for associating a position in the image of the first distribution information with a position in the image of the second distribution information, as illustrated in FIG. 6. Similar to the first exemplary embodiment, it is preferable that the user can select either one of the mode in which the position associating guides are displayed and the mode in which the position associating guides are not displayed.

Also in the present exemplary embodiment, it is preferable that the display control unit 008 is provided with either one of the single display mode and the superimposed display mode, in addition to the above-described parallel display mode in which the images are displayed in parallel.

The effect of an embodiment of the present invention can also be obtained by displaying the combined image of the first and second distribution information in parallel with the image of the first distribution information.

In a third exemplary embodiment, the display control unit 008 first displays the image of the first distribution information. Then, upon reception of information about a specified area in the image of the first distribution information, the display control unit 008 enlarges the image of the first distribution information at the position of the specified area, and the image of the second distribution information or the combined image of the first and second distribution information at a position corresponding to the specified area to display these enlarged images in parallel. Other processing is similar to that according to the first and second exemplary embodiments. The object information acquisition apparatus according to the present exemplary embodiment has a similar configuration to that of the apparatus illustrated in FIG. 1.

Figure 7:
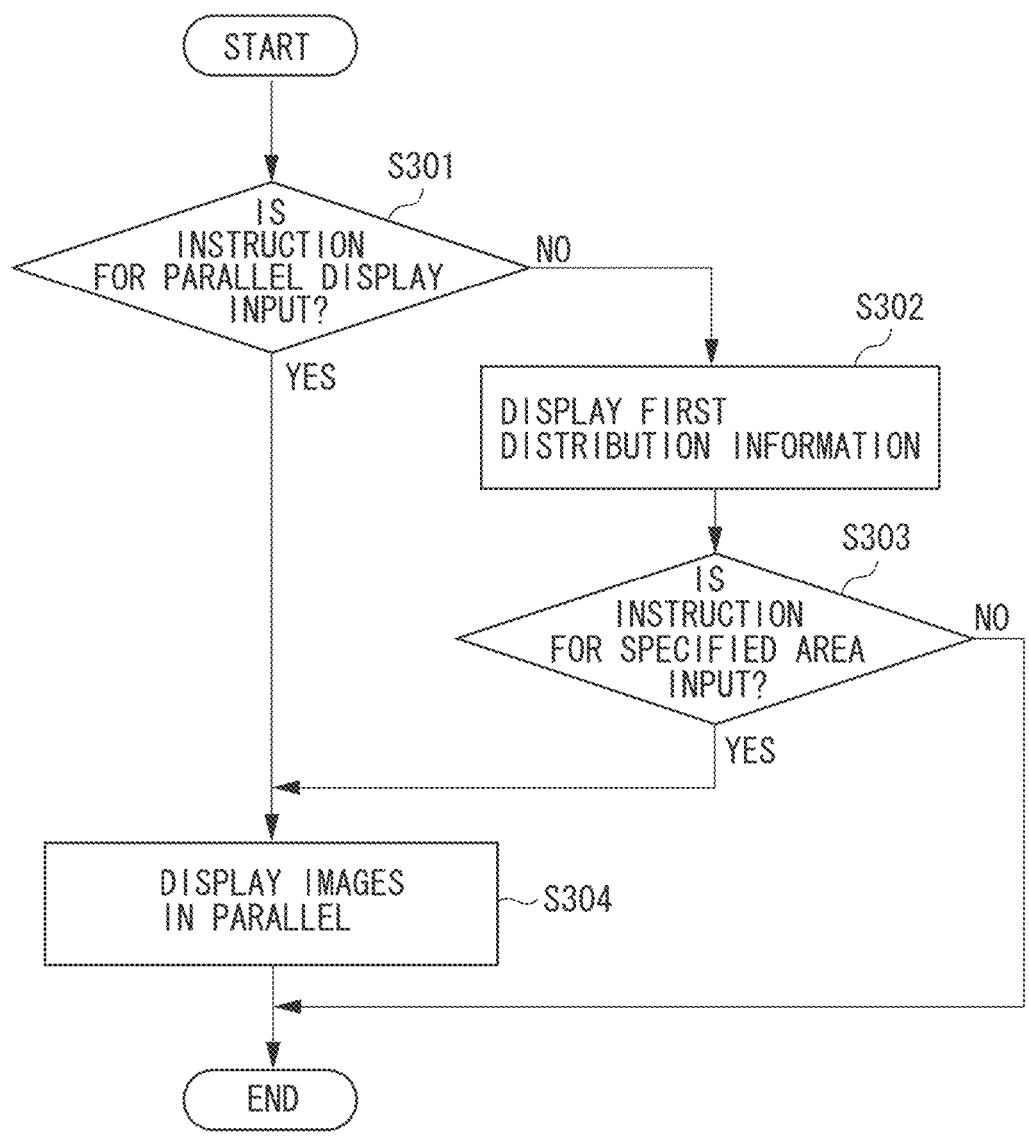
FIG. 7 is a flowchart illustrating processing of a display method according to a third exemplary embodiment.

Processing performed by a display method according to the present exemplary embodiment will be described below with reference to FIG. 7. FIG. 7 is a flowchart illustrating the display method according to the present exemplary embodiment. According to the present exemplary embodiment described below, the image of the first distribution information and the image of the second distribution information are enlarged and displayed in parallel.

Instep S301, the display control unit 008 determines whether a parallel display instruction (parallel display instruction information) is input from the user. When a parallel display instruction is input (YES in step S301), then in step S304, the display control unit 008 outputs image information for displaying in parallel within the same screen the image of the first distribution information and the image of the second distribution information, similar to the first exemplary embodiment.

When a parallel display instruction is not input (NO in step S301), then in step S302, the display control unit 008 outputs image information for singly displaying the image of the first distribution information to the display unit 009. Based on this image information, the display unit 009 displays the image of the first distribution information.

Instep S303, the display control unit 008 determines whether an indication of a specified area (information about the specified area) is input from the user. The user inputs the specified area as an area to be enlarged (hereinafter referred to as an enlargement area), by using the input unit 010, such as a mouse, while monitoring the image of the first distribution information displayed on the display unit 009. The system control unit 004 inputs the information about the specified area from the input unit 010, and outputs the information about the specified area to the display control unit 008 as information about an enlargement instruction from the user. Thus, to specify an enlargement area, the user inputs an enlargement instruction by specifying a desired area in the image of the first distribution information. Then, the display control unit 008 determines the enlargement rate of the enlarged image based on the relation between the size of the area specified by the user and the size of the display area of the display unit 009. It is also preferable to input an enlargement start instruction after the user specifies an enlargement area and then clicks the ENLARGE button (refer to FIG. 8) displayed on the screen of the display unit 009.

Figure 8:
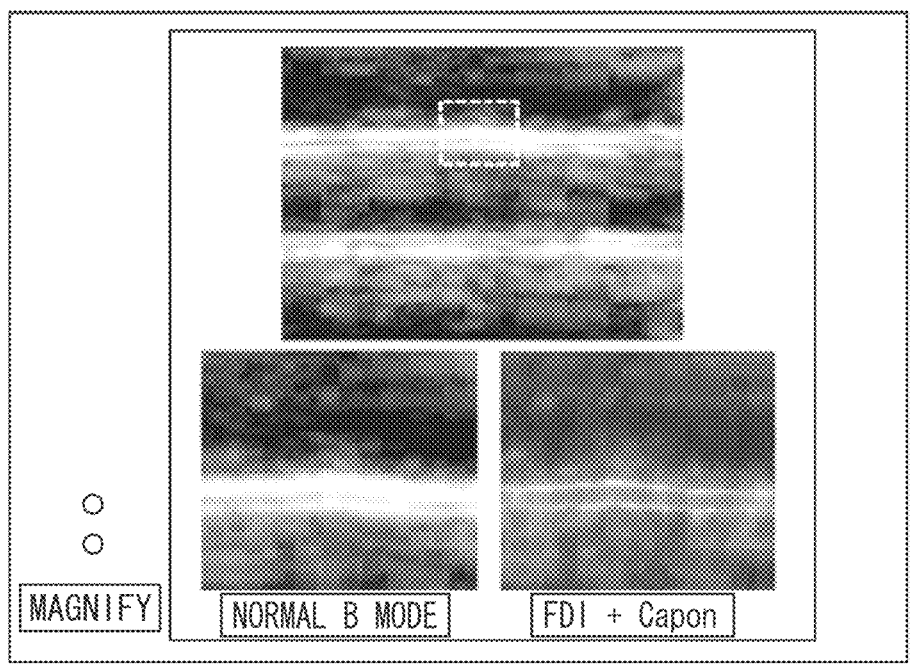
FIG. 8 illustrates an example screen displayed on the display unit according to third exemplary embodiment.

When an instruction for a specified area is input (YES in step S303), then in step S304, the display control unit 008 displays in parallel an enlarged version of the image of the first distribution information at the position of the specified area and an enlarged version of the image of the second distribution information at a position corresponding to the specified area. FIG. 8 illustrates an example screen displayed on the display unit 009 according to the present exemplary embodiment.

FIG. 8 illustrate the layer structure of the blood vessel wall. In the example screen, the image at the top is the image before enlargement (the image of the first distribution information), the image at the bottom left is an enlarged version of the image of the first distribution information in the specified area (normal B mode), and the image at the bottom right is an enlarged version of the image of the second distribution information in the specified area (FDI+Capon). In the example illustrated in FIG. 8, the display control unit 008 performs processing combining the FDI method and the Capon method as adaptive signal processing (the example illustrated in FIG. 3B) to acquire an image of the second distribution information. This processing enables providing more user-friendly display by enlarging the image of the first distribution information and the image of the second distribution information, and displaying the two images in parallel. Depending on enlargement rate, image visibility may not be improved because of an inferior resolution even if the image of the first distribution information is simply enlarged. In this case, if an enlarged version of the image of the second distribution information having a sufficient resolution acquired through adaptive signal processing is displayed, image visibility can be improved. Further, by displaying the enlarged version of the image of the second distribution information in parallel with the enlarged version of the image of the first distribution information, the comparison between the two enlarged images is facilitated.

Referring to FIG. 8, the screen displays the above-described ENLARGE button. When the user clicks the ENLARGE button with an enlargement area specified (in a state where information about enlargement instruction has been input to the display control unit 008), an enlargement start instruction is input to the display control unit 008. Upon reception of the enlargement start instruction, the display control unit 008 outputs to the display unit 009 image information for displaying in parallel an enlarged version of the image of the first distribution information and an enlarged version of the image of the second distribution information. It is preferable that the screen of the display unit 009 is switched over based on the image information.

In the present exemplary embodiment, the display control unit 008 also displays, a thumbnail of the image of the first distribution information before enlargement, in another display area (top area illustrated in FIG. 8) of the screen which displays these enlarged images. A rectangle enclosed by dotted lines indicates the position on the image of the first distribution information corresponding to the enlarged image (the position of the enlargement area on the image of the first distribution information). By displaying a guide for indicating the position of the enlarged area like this rectangle, it becomes easier for the user to grasp the position of the enlarged image.

It is also possible that the position of the enlargement area can be changed when the user moves the guide indicating the position of the enlargement area. When a guide movement instruction is input from the user to the system control unit 004 via the input unit 010, the system control unit 004 outputs guide movement information to the display control unit 008. Upon reception of the guide movement information, the display control unit 008 moves the guide on the screen, and displays on the display unit 009, an enlarged version of the image moved to the changed enlargement area.

It is also possible that the size of the enlargement area (i.e., the enlargement rate) can be changed when the user changes the size of the guide. When a guide size change instruction is input from the user to the system control unit 004 via the input unit 010, the system control unit 004 outputs size change information to the display control unit 008. Upon reception of the guide size change information, the display control unit 008 changes the size of the guide on the screen, and displays on the display unit 009 an enlarged version of the image moved to the changed enlargement area. Since the position and size of the guide can be changed in this way, the user can easily change the position and size of an area inside the object the user wants to enlarge and observe, thus improving the operability.

Also in the present exemplary embodiment, it is also possible to display guides for associating a position in the image of the first distribution information with a position in the image of the second distribution information. Of course, similar to the first exemplary embodiment, it is preferable that the user can select either one of the mode in which the position associating guides are displayed and the mode in which the position associating guides are not displayed.

Also in the present exemplary embodiment, it is preferable that the display control unit 008 is provided with either one of the single display mode and the superimposed display mode, in addition to the above-described parallel display mode in which the images are displayed in parallel.

The effect of an embodiment of the present invention can also be obtained by displaying the combined image of the first and second distribution information in parallel with the image of the first distribution information.

In a fourth exemplary embodiment, the display control unit 008 displays in parallel the image of the first distribution information and the combined image of the first and second distribution information when parallel display instruction information is input. Other processing is similar to that according to the first to third exemplary embodiments. The object information acquisition apparatus according to the present exemplary embodiment has a similar configuration to that of the apparatus illustrated in FIG. 1. The overview of the display method is basically the same as the processing described with reference to FIG. 4.

In the present exemplary embodiment, upon reception of the parallel display instruction information from the user, the display control unit 008 displays in step S102 the image of the first distribution information and the combined image of the first and second distribution information. The combination rate for the image of the first distribution information and the image of the second distribution information may be predetermined like 50:50, or arbitrarily set by the user.

Figure 9:
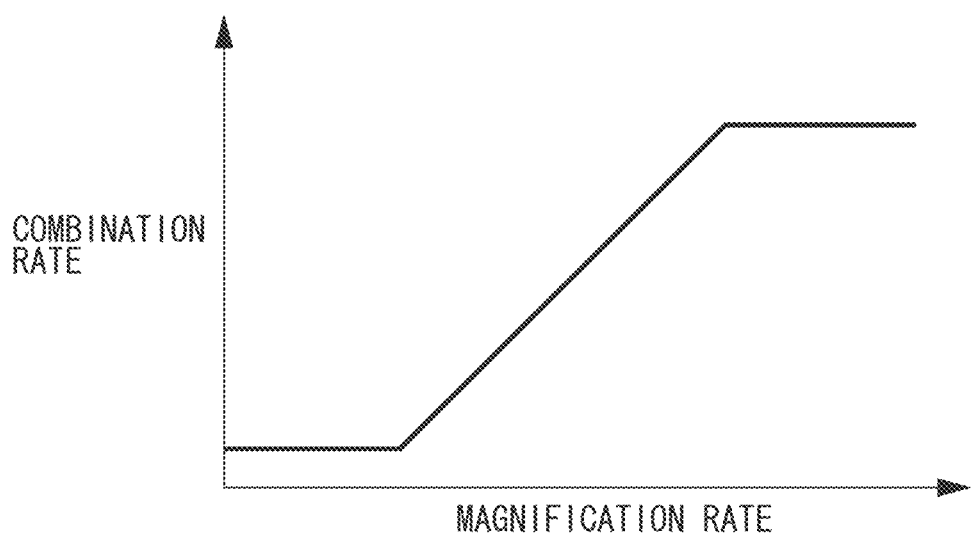
FIG. 9 illustrates a relation between the enlargement rate and the combination rate according to a fourth exemplary embodiment.

Further, similar to the third exemplary embodiment, when enlarging the image in a specified area, the combination rate may be changed according to the enlargement rate. FIG. 9 illustrates an example relation between the enlargement rate and the combination rate. Referring to FIG. 9, when the enlargement rate is below a first predetermined value, the display control unit 008 maintains constant the combination rate for the first and second distribution information. In this case, because of a low enlargement rate, the combination rate for the image of the second distribution information is low (i.e., the ratio of the image of the first distribution information is high, and the ratio of the image of the second distribution information is low in the combined image). When the enlargement rate is higher than the first predetermined value and lower than a second predetermined value, the display control unit 008 increases the combination rate for the image of the second distribution information (the ratio of the image of the second distribution information to the image of the first distribution information in the combined image) as the enlargement rate increases. When the enlargement rate is equal to or higher than the second predetermined value, the display control unit 008 maintains constant the combination rate for the first and second distribution information. In this case, because of a high enlargement rate, the display control unit 008 increases the combination rate for the image of the second distribution information.

According to an embodiment of the present invention, it is possible to provide user-friendly display method and object information acquisition apparatus when displaying an image generated through adaptive signal processing.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-187618 filed Aug. 28, 2012, which is hereby incorporated by reference herein in its entirety.

What is claimed is:

1. An object information acquisition apparatus comprising:
    a plurality of conversion elements configured to transmit elastic waves to an object, receive waves reflected at each position inside the object, and convert the reflected waves into a plurality of received signals;

a fixed signal processing unit configured to apply addition with a predetermined weight to the plurality of received signals to acquire first distribution information;

an adaptive signal processing unit configured to apply adaptive signal processing to the plurality of received signals with a weight which adaptively changes according to the received signals to acquire second distribution information; and a display control unit configured to input the first distribution information and the second distribution information, and output image information to a display unit, wherein the display control unit outputs image information for displaying in parallel in the same screen an image of the first distribution information, and an image of the second distribution information or a combined image of the first and second distribution information.

2. The object information acquisition apparatus according to claim 1, wherein the display control unit displays guides for associating a predetermined position in the image of the first distribution information with a position corresponding to the predetermined position in the image of the second distribution information or in the combined image.

3. The object information acquisition apparatus according to claim 1, wherein the display control unit is configured to selectively execute the following modes:

a mode for displaying in parallel the image of the first distribution information, and the image of the second distribution information or the combined image, and at least either one of a mode for singly displaying either one of the image of the first distribution information, the image of the second distribution information, and the combined image, and a mode for superimposing the image of the first distribution information with the image of the second distribution information or the combined image.

4. The object information acquisition apparatus according to claim 1, wherein the display control unit changes a way of arrangement when the image of the first distribution information and the image of the second distribution information are displayed in parallel, according to the adaptive signal processing method.

5. The object information acquisition apparatus according to claim 1, wherein the adaptive signal processing unit applies processing to the plurality of received signals so that the electric power is minimized in a state where sensitivity for target directions is fixed, and wherein the display control unit displays in parallel the image of the first distribution information, and the image of the second distribution information or the combined image so that the images are arranged in the same direction as the depth direction in the image of the second distribution information or the combined image.

6. The object information acquisition apparatus according to claim 1, wherein the adaptive signal processing unit applies processing to the plurality of received signals so that the electric power is minimized in a state where sensitivity for target positions is fixed in the depth direction, and wherein the display control unit displays in parallel the image of the first distribution information, and the image of the second distribution information or the combined image so that the images are arranged in the direction perpendicular to the depth direction within the image of the second distribution information or the combined image.

7. The object information acquisition apparatus according to claim 1, wherein the display control unit receives information of a specified area in the image of the first distribution information input by the user in a state where only the first distribution information, out of the image of the first distribution information and the image of the second distribution information, is displayed; and wherein the display control unit displays in parallel an enlarged version of the image of the first distribution information at the position of the specified area, and an enlarged version of the image of the second distribution information or the combined image at a position corresponding to the specified area.

8. The object information acquisition apparatus according to claim 7, wherein display control unit receives information of a specified area in the image of the first distribution information input by the user; and displays a guide for indicating a specified area in the image of the first distribution information.

9. A display method for displaying an image on a display unit by using distribution information acquired by an object information acquisition apparatus, wherein the acquired distribution information includes:

first distribution information acquired by applying addition with a predetermined weight to a plurality of received signals obtained by transmitting elastic waves to an object and receiving reflected waves reflected by the object, and second distribution information acquired by applying to the plurality of received signals adaptive signal processing with a weight which adaptively changes according to the received signals, wherein the image of the first distribution information, and the image of the second distribution information or the combined image of the first and second distribution information are displayed in parallel in the same screen.

10. The display method according to claim 9, further comprising:

displaying guides for associating a predetermined position in the image of the first distribution information, with a position corresponding to the predetermined position in the image of the second distribution information or the combined image.

11. The display method according to claim 9, wherein the following modes are selectively executable:

a mode for displaying in parallel the image of the first distribution information, and the image of the second distribution information or the combined image, and at least either one of a mode for singly displaying either one of the image of the first distribution information, the image of the second distribution information, and the combined image, and a mode for superimposing the image of the first distribution information with the image of the second distribution information or the combined image.

12. The display method according to claim 9, wherein, in the parallel display, a way of arrangement in parallel display of the image of the first distribution information and the image of the second distribution information is changed according to the adaptive signal processing method.

13. The display method according to claim 9, wherein the second distribution information is acquired by applying adaptive signal processing to the plurality of received signals so that the electric power is minimized in a state where sensitivity for target directions is fixed, and wherein, in the parallel display, the image of the first distribution information, and the image of the second distribution information or the combined image are arranged in the same direction as the depth direction in the image of the second distribution information or the combined image.

14. The display method according to claim 9, wherein the second distribution information is acquired by applying adaptive signal processing to the plurality of received signals so that the electric power is minimized in a state where sensitivity for target positions is fixed in the depth direction, and wherein, in the parallel display, the image of the first distribution information, and the image of the second distribution information or the combined image are displayed in parallel so that the images are arranged in the direction perpendicular to the depth direction within the image of the second distribution information or the combined image.

15. The display method according to claim 9, further comprising:

displaying only the image of the first distribution information, out of the image of the first distribution information and the image of the second distribution information before making the parallel display, wherein the parallel display displays the following in parallel:

an enlarged version of the image of the first distribution information at a position of the specified area within the image of the first distribution information input by the user, and an enlarged version of the image of the second distribution information or the combined image at a position corresponding to the specified area.

16. The display method according to claim 15, further comprising:

displaying a guide indicating a specified area within the image of the first distribution information input by the user.

17. A computer readable storage medium storing a program for causing a computer to execute the display method according to claim 9.

18. A display method for displaying an image on a display unit by using distribution information acquired by an object information acquisition apparatus, wherein the acquired distribution information includes:

first distribution information acquired by applying addition with a predetermined weight to a plurality of received signals obtained by transmitting elastic waves to an object and receiving reflected waves reflected by the object, and second distribution information acquired by applying to the plurality of received signals adaptive signal processing with a weight which adaptively changes according to the received signals, wherein the method includes displaying in parallel in the same screen, in a case where an instruction of parallel display is input, an image of the first distribution information, and the image of the second distribution information or a combined image of the first and second distribution information.

19. The display method according to claim 18, wherein the method includes displaying the image of the first distribution information in a case where an instruction of parallel display is not input.

20. The display method according to claim 19, wherein the method includes displaying in parallel, in the case where the instruction of parallel display is not input, and in a case where a designation of an area within the image of the first distribution information is input, an enlarged version of the image of the first distribution information for the designated area and an enlarged version of the image of the second distribution or a combined image of the first and second distribution information for an area corresponding to the designated area.

21. The display method according to claim 20, wherein in the case where an enlarged version of the combined image of the first and second distribution information is displayed, a combination ratio of the first and second distribution information is determined based on a size of the designated area.

22. The display method according to claim 18, wherein the method further includes displaying an indication of the image of the first distribution information and the image of the second distribution or a combined image of the first and second distribution information.

23. The object information acquiring apparatus according to claim 1, wherein the display control unit outputs information for further displaying an indication of the image of the first distribution information and the image of the second distribution information or a combined image of the first and second distribution information.

24. The display method according to claim 9, wherein the method further includes displaying an indication of the image of the first distribution information and the image of the second distribution information or a combined image of the first and second distribution information.

* * * * *